(12) United States Patent
Ge et al.

(10) Patent No.: US 9,829,309 B2
(45) Date of Patent: Nov. 28, 2017

(54) DEPTH SENSING METHOD, DEVICE AND SYSTEM BASED ON SYMBOLS ARRAY PLANE STRUCTURED LIGHT

(71) Applicant: RGBDsense Information Technology Ltd., Ningbo (CN)

(72) Inventors: Chenyang Ge, Xi'an (CN); Yanhui Zhou, Xi'an (CN)

(73) Assignee: RGBDsense Information Technology Ltd., Ningbo (CN)

( * ) Notice: Subject to any disclaimer, the term of this patent is extended or adjusted under 35 U.S.C. 154(b) by 276 days.

(21) Appl. No.: 14/807,433

(22) Filed: Jul. 23, 2015

(65) Prior Publication Data

US 2016/0178355 A1 Jun. 23, 2016

(30) Foreign Application Priority Data

Dec. 23, 2014 (CN) .......................... 2014 1 0810399

(51) Int. Cl.
*G01B 11/00* (2006.01)
*G01B 11/22* (2006.01)
(Continued)

(52) U.S. Cl.
CPC ............ *G01B 11/22* (2013.01); *G01B 11/254* (2013.01); *G06K 9/2036* (2013.01);
(Continued)

(58) Field of Classification Search
None
See application file for complete search history.

(56) References Cited

U.S. PATENT DOCUMENTS 6,542,249 B1 * 4/2003 Kofman ............ G01B 11/2513
356/601
6,549,288 B1 * 4/2003 Migdal .................. G01B 11/25
356/601

(Continued)

*Primary Examiner* — Joseph Ustaris
*Assistant Examiner* — William Adrovel
(74) *Attorney, Agent, or Firm* — Birch, Stewart, Kolasch & Birch, LLP

(57) ABSTRACT

The present invention discloses a depth sensing method, device and system based on symbols array plane structured light. The coded symbols array pattern is projected by the laser pattern projector to the target object or space, and the image sensor collects and obtains the successive sequence of the encoded image of the input symbols. Firstly, the input image encoded with the symbols is decoded. The decoding process includes preprocessing, symbols location, symbols recognition and symbols correction. Secondly, the disparity of the decoded symbols are calculated by the symbols match calculation between the decoded image of the input symbols with completed symbols recognition and the decoded image of the reference symbols with the known distance. Finally the depth calculation formula is combined to generate depth point cloud information of the target object or projection space that is represented in the form of grid. The present invention can quickly obtain high-resolution and high-precision depth information of the target object or projection space in dynamic scenes, which facilitates the porting or insertion as a module into the intelligent device for 3D modeling, 3D mapping, etc.

17 Claims, 5 Drawing Sheets

(51) Int. Cl.

| | | |
|---|---|---|
| *G01B 11/25* | (2006.01) | |
| *G01B 11/26* | (2006.01) | |
| *G06T 7/50* | (2017.01) | |
| *G06T 7/521* | (2017.01) | |
| *G06T 7/593* | (2017.01) | |
| *G06K 9/20* | (2006.01) | |
| *G01S 17/06* | (2006.01) | |
| *H04N 13/02* | (2006.01) | |
| *H04N 19/597* | (2014.01) | |
| *G06K 9/62* | (2006.01) | |
| *A61B 5/00* | (2006.01) | |
| *A61B 5/107* | (2006.01) | |

(52) U.S. Cl.
CPC ............ *G06K 9/6203* (2013.01); *G06T 7/521* (2017.01); *A61B 5/0062* (2013.01); *A61B 5/1077* (2013.01); *G01B 11/00* (2013.01); *G01B 11/25* (2013.01); *G01B 11/2513* (2013.01); *G01B 11/2518* (2013.01); *G01B 11/26* (2013.01); *G01S 17/06* (2013.01); *G06K 2009/2045* (2013.01); *G06T 7/50* (2017.01); *G06T 7/593* (2017.01); *G06T 2207/10028* (2013.01); *H04N 13/0253* (2013.01); *H04N 19/597* (2014.11)

(56) References Cited

U.S. PATENT DOCUMENTS

| | | | |
|---|---|---|---|
| 2004/0125205 A1* | 7/2004 | Geng | G01B 11/2509 348/142 |
| 2004/0222987 A1* | 11/2004 | Chang | G01B 11/2509 345/419 |
| 2009/0161966 A1* | 6/2009 | Lim | G06K 9/2036 382/209 |
| 2009/0221874 A1* | 9/2009 | Vinther | A61B 5/0062 600/178 |
| 2011/0134225 A1* | 6/2011 | Saint-Pierre | G01B 11/03 348/47 |
| 2011/0221891 A1* | 9/2011 | Sonoda | G01B 11/2513 348/135 |
| 2012/0293626 A1* | 11/2012 | Lee | G06T 7/521 348/46 |
| 2012/0327430 A1* | 12/2012 | Lee | G01B 11/2513 356/625 |
| 2014/0002610 A1* | 1/2014 | Xi | G01B 11/2513 348/46 |
| 2014/0037146 A1* | 2/2014 | Taguchi | G01B 11/2509 382/107 |
| 2014/0104416 A1* | 4/2014 | Giordano | G01B 11/02 348/135 |
| 2015/0145959 A1* | 5/2015 | Tang | G06K 9/00711 348/46 |

* cited by examiner

Unidentified symbol represented with 16 a. Example of symbol encoding rule
b. Example of encoded image of input symbol
c. Primary symbol correction result
d. Cyclic symbol correction and filling result Decoded image of input symbols Decoded image of reference symbols

DEPTH SENSING METHOD, DEVICE AND SYSTEM BASED ON SYMBOLS ARRAY PLANE STRUCTURED LIGHT

FILED OF THE INVENTION

The present invention belongs to the technical fields of pattern recognition, human-computer interaction, 3D reconstruction and machine vision technology. More specifically, it relates to a depth sensing method, device and system based on symbols array plane structured light.

BACKGROUND OF THE INVENTION

In the field of consumer electronics, depth sensing technology helps to improve the intelligence level and interaction ability of electronic products and helps intelligent terminals to understand human actions, so that it has become one of the interactive tools between the "real physical world" and the "virtual network world", which could not only realize innovative applications in the fields of smart TV, smart phones, home appliances, tablet PC, etc., but also be used in intelligent video monitoring, facial identification system, 3D animation, dynamic scene detection and 3D reconstruction such as real-time 3D mapping. In industrial field, there is a wide range of application needs for high-resolution and high-precision 3D depth information in the fields such as auto-aided safe driving, high-speed machining, industrial 3D modeling, 3D printing, medical imaging, Internet of Things 3D visual sensing and robotic control.

The depth sensing technology based on the active vision pattern of structured light (the laser pattern projector actively projects graphics pattern and the image sensor captures continuous images) can more accurately obtain the depth information of the target object or projection space, and compared to the binocular stereo camera, this model that uses encoded structured light to actively calibrate the features of the projection object or projection space, which has advantages of acquiring more stable and reliable depth map information, being less affected by ambient light, and not being affected by object's texture information in the match process. For example, Kinect actively projects the infrared laser speckle images to calibrate features, the infrared camera captures the infrared image sequence, and then the depth sensing chip computes and acquires depth information. However, Kinect uses DoE diffraction to generate the laser speckle image, which is difficult to obtain high-resolution and high-precision depth information and difficult to meet the needs of applications in industrial modeling field, etc., and has unavailable ability to self-correcting the improper depth values or holes. At the same time, the existing technologies of structured light encoding depth sensing and 3D measurement are difficult to acquire real-time high-resolution and high-precision depth information of the target object in the dynamic scene.

SUMMARY OF THE INVENTION

In view of this, the purpose of the present invention is to provide a depth sensing method, device and system based on symbols array plane structured light. Based on the active visual pattern of structured light encoding, the coded symbols array pattern in line with the array structure is projected by the laser pattern projector to the target object or projection space, and the image sensor collects and obtains the successive sequence of the encoded image of the input symbols. At first, the input image encoded with the input symbols is decoded. The decoding process includes preprocessing, symbols location, symbols recognition and symbols correction. Then the symbols match calculation is conducted between the decoded image of the input symbols with completed symbols recognition and the decoded image of the reference symbols of the known distance to obtain the disparity. Finally the depth calculation formula is combined to generate depth point cloud information in the form of grid that represents the target object or projection space.

According to the present invention, a depth sensing method based on symbols array plane structured light comprising:

obtaining encoded image of the input symbols of the said symbols array plane structured light;

adaptively preprocessing the encoded image of the input symbols;

performing symbols location of the pre-processed encoded image of the input symbols, that is, to identify the location of the center of all symbols in the said coded image of the input symbols;

conducting symbols recognition of the preprocessed encoded image of the input symbols, mapped as the corresponding number of the code word;

correcting identified symbols in accordance with the corresponding number to complete the decoding of the encoded image of the input symbols;

calculating the disparity of the symbols by making symbols match between the corrected decoded image of the input symbols and the decoded image of the reference symbols with the known distance;

determining depth of the center of the symbols in the said encoded image of the input symbols in accordance with the known distance of the said decoded image of the reference symbols and the said disparity value.

Preferably, performing the symbols location of the preprocessed encoded image of the input symbols, that is, to identify the location of the center of all symbols in the said coded image of the input symbols, including: computing the location of the center of symbols one by one in accordance with the design parameters or determining that in accordance with the feature information of the symbols and by means of pattern identification.

Preferably, recognizing the symbols contains a template matching method that takes the code symbols as the standard match symbols template rotating at a small angle around the center of the symbols or identifying the code symbols of the encoded image of the input symbols after linear or non-linear transformation of the symbols.

Preferably, recognizing the symbols contains a SVM pattern identification method based on sample training.

Preferably, said mapping on the corresponding numbers, comprises: the correct symbols identified are mapped on a specific number N, and the unidentified symbols is represented with a specific number M.

Preferably, correcting the identified symbols in accordance with the corresponding number comprises validating the identified symbols in combination with its surrounding symbols and by means of the coding rule of the said symbols.

Preferably, identifying the symbols conforming to the said encoding rule as correct one, while representing the symbols inconsistent with the coding rule with the specific number M as unidentified one for further correction, which after cyclic correction fill the corrected decoded image of the input symbols.

Preferably, matching the symbols between the corrected decoded image of the input symbols and the decoded image of the reference symbols of the known distance comprises searching for the closest match symbols of the input symbols within a certain range taking the symbols of the corresponding location of the input symbols in the decoded image of the reference symbols as the center.

Preferably, performing the symbols match between the corrected decoded of the input symbols and the decoded image of the reference symbols of the known distance, comprises that the input symbols and its surrounding symbols form an input symbols template to search for the optimal match template in the search window of the decoded image of the reference symbols to obtain the matching symbols of the input symbols so as to obtain the disparity ($\Delta x$, $\Delta y$) between the input symbols and the matched reference symbols;

Preferably, the depth of the center of the symbols in the encoded image of the input symbols comprises calculating the depth information d' of the center o of the input symbols according to the following formula by means of the disparity $\Delta m$ ($\Delta x$ or $\Delta y$) at the direction X or Y and in combination with the known distance parameter d of the decoded image of the reference symbols, the baseline distance S between the laser pattern projector and the image sensor, the focal length f and the pixel pitch parameter $\mu$ of the image sensor:

$$d' = d - \frac{\Delta m \mu d^2}{fS + \Delta m \mu d} = \frac{fSd}{fS + \Delta m \mu d}$$

The present invention can quickly obtain high-resolution and high-precision depth information of the target object or projection space in the dynamic scene, which can be programmatically ported to different hardware platforms and operating systems and easily integrated into chips through hardware. The threshold for the integrated depth sensing module of the intelligent device to obtain depth information with high-resolution and high-precision is reduced, which makes it possible for smart devices (mobile devices such as smart phone and tablet PC) to achieve real-time 3D scanning, 3D modeling and real-time 3D mapping. The beneficial effect of the technical solution of the present invention is also specially expressed in the description of the following embodiments.

Accordingly, the present invention also includes a depth sensing device for symbols array plane structured light and a system comprising said device.

DETAILED DESCRIPTION OF THE INVENTION

The present invention will be described in further detail in combination with the drawings.

Figure 1:
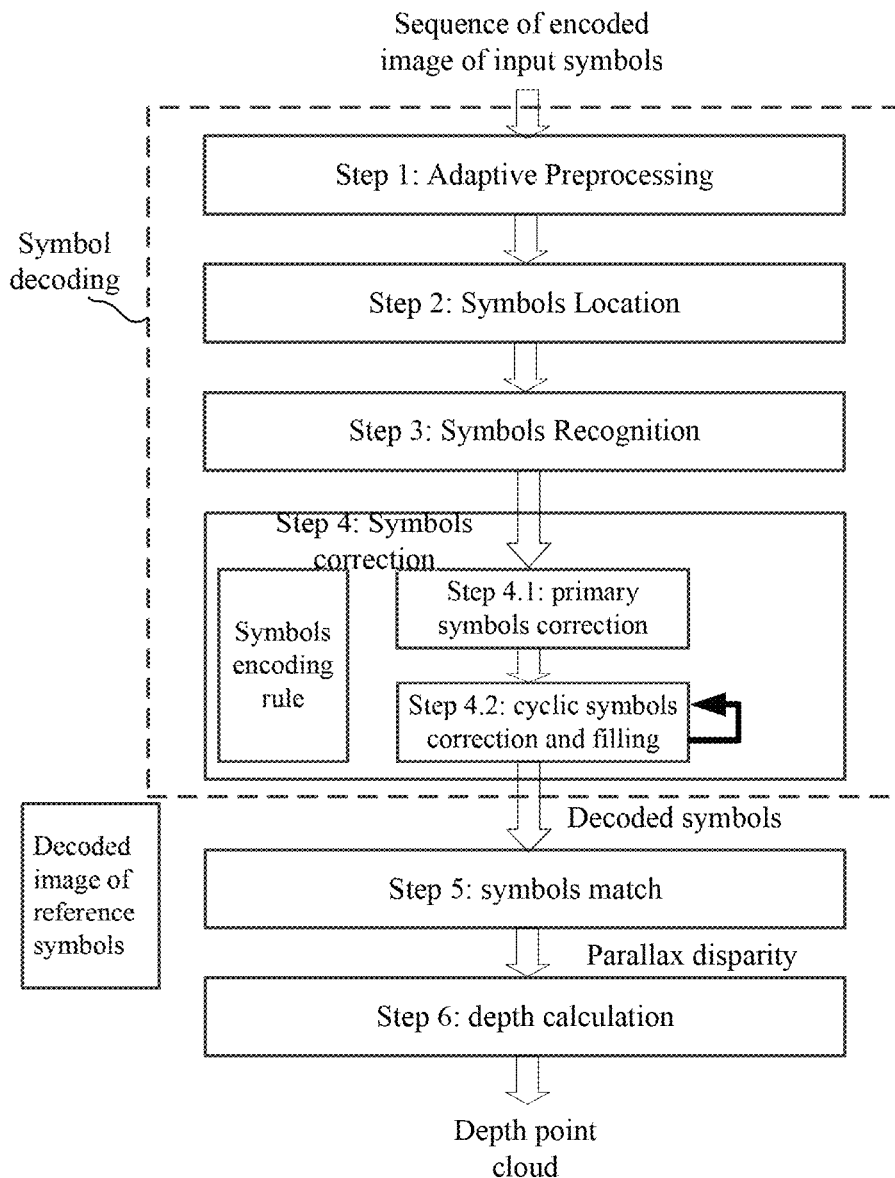
FIG. 1 is a overall flow chart according to an embodiment of the present invention.

FIG. 1 schematically illustrates a overall flow chart of a depth sensing of symbols array plane structured light according to an embodiment of the present invention. For clarity, the method will be described hereinafter in combination with FIG. 2, FIG. 3, FIG. 4, FIG. 5, FIG. 6, FIG. 7, FIG. 8, FIG. 9 and FIG. 10

The laser pattern projector is a projecting device of laser encoded graphical pattern, the projected pattern may be fixed or can be changed programmatically; the projection can be in the synchronized control with the reception by the image sensor; the projected patterns have a certain horizontal and vertical viewing angle FoV; the laser light source may be visible light, infrared light, ultraviolet or X-ray.

The code symbols refer to symbols that are regular and have the same size, such as numbers, letters and symbols with specific shapes. The code symbols can be distinguished from each other due to the uniqueness, and at the same time, they can be connected in series with each other.

The said encoded image of the input symbols is collected and obtained by the image sensor and formed by the organic permutation of a number of code symbols according to certain rules. The image is projected by the laser pattern projector to the target object or projection space for the calibration of feature and then collected and obtained by the image sensor. It is generally constituted of the same code symbols in the horizontal direction, but the upper and lower code symbols are different. With the overall rotation at a certain angle, the code symbols in a certain range in the horizontal or vertical direction have no repetition.

For the said decoded image of the reference symbols the laser beam of the fixed graphic pattern is projected by the laser projector (infrared, visible light, ultraviolet light or black light) onto the plane (the plane may consists of the projection screen, tablet, etc. presenting clear and stable laser images, which can be called reference datum plane) with the known vertical distance d, perpendicular to or at a fixed angle to central axis (Z axis) of the laser pattern projector, and then being collected and obtained by the image sensor. After the same adaptive preprocessing, symbols location, symbols recognition and symbols correction as the encoded image of the input symbols, the decoded image of the reference symbols which is taken as the datum match graphics for symbols match computation of the encoded image of the reference symbols can be constituted of one or more encoded images of laser symbols at different distances.

The said decoded image of the input symbols is a symbols image output from the encoded image of the input symbols after adaptive preprocessing, symbols location, symbols recognition and one or more symbols correction after filling, namely the decoded image.

A depth sensing method for symbols array plane structured light according to the present invention comprises following steps (as shown in FIG. 1):

Step 1: adaptive preprocessing. Adaptively preprocessing the encoded image of the input symbols collected and obtained by the image sensor results in uniform features of the sequence of the encoded image of the input symbols, including enhancing, de-noising, removing background light impact, etc.

Figure 2:
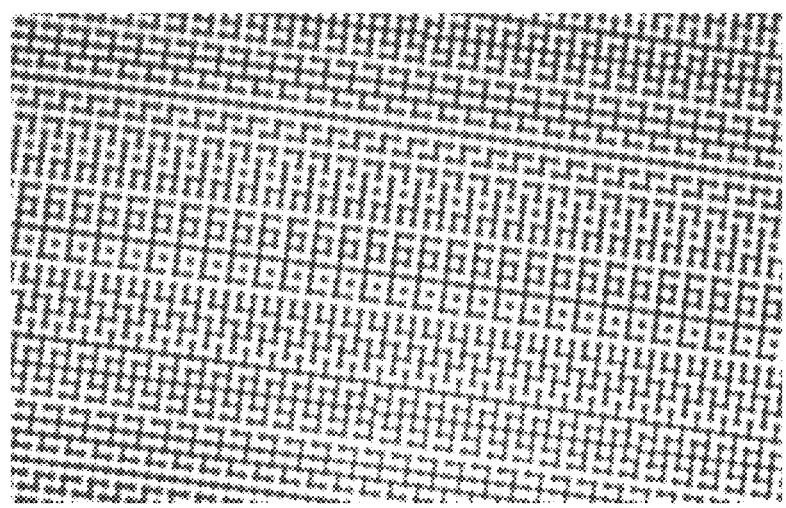
FIG. 2 is a schematic diagram of a symbol-encoded image according to an embodiment of the present invention.

Wherein, the encoded image of the input symbols is formed by arranging a number of code symbols in certain organic permutation, as shown in FIG. 2, which is projected by the laser projector to the target object or projection space for feature calibration and then collected and obtained by the image sensor. The permutated code symbols have no repetition within a certain range at the horizontal or vertical direction.

The adaptive preprocessing process includes input video format conversion (e.g. interface format conversion of Bayer, ITU601, ITU656 and MIPI), color space conversion (e.g. RGB to YUV), gray image consistency enhancement and gray image binarization (direct gray image processing without performing binarization is also possible). The adaptive preprocessing makes clearer encoded image of the input symbols collected, reduces noise and light impact and enhances the consistency of the sequence of the encoded image of the input symbols, which is favorable to the symbols recognition, symbols correction and depth calculation of the present invention.

Step 2: symbols location. The symbols location of the preprocessed encoded image of the input symbols can be performed to identify the location of the center of symbols. Due to the same size of the symbols used in the encoding process, the location of the center of symbols in the coded image of the input symbols can be calculated one by one based on the design parameters (symbols size, symbols permutation rule, symbols inclination angle, etc.) or determined on the basis of the symbols feature information and by means of the pattern identification method.

Step 3: symbols recognition. The symbols recognition of the preprocessed encoded image of the input symbols can be conducted, and the correct symbols is identified and mapped on one specific number N, that is, the symbols are represented with the number, while the unidentified symbols are represented with the specific number M.

Figure 3:
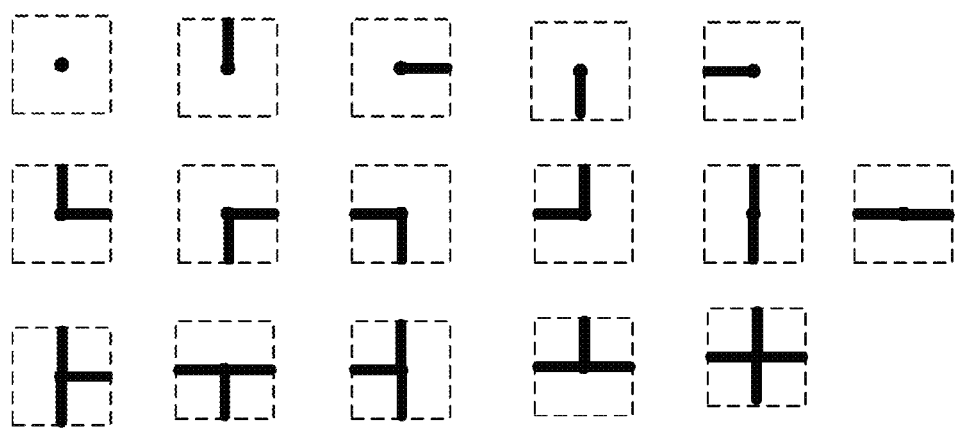
FIG. 3 is a schematic diagram of encoding symbols according to an embodiment of the present invention.

FIG. 3 is a schematic diagram of encoded symbols according to an embodiment of the present invention. There are 16 kinds of code symbols and each kind consists of points and lines in different permutations. They can be distinguished from each other due to the uniqueness, but they can be connected in series with each other. Different code symbols have the same size. FIG. 3 illustrates only one embodiment of the present invention. The code symbols may also consist of other types of symbols, which, in spite of different shape and number of symbols, are within the scope of the present invention.

Figure 4:
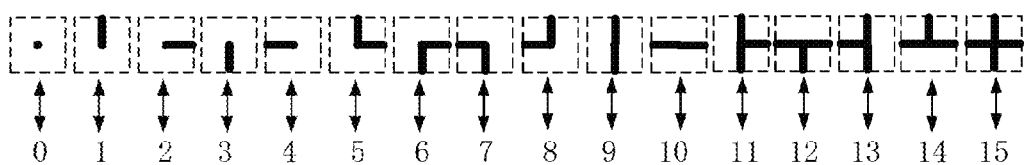
FIG. 4 illustrates a mapping relation between symbols and numbers according to an embodiment of the present invention.

FIG. 4 illustrates the mapping relation between the 16 kinds of code symbols and the numbers of 0-15 according to an embodiment of the present invention. The unidentified code symbols (i.e., the symbols inconsistent with the rule of the16 kinds of code symbols in the identification process, which is because the projected laser graphics is absorbed or shielded by the target object, the distance of the object is too far, or the adaptive preprocessing has defects) can be represented with the number 16. FIG. 4 illustrates only one exemplary embodiment of the present invention, the number is only used to distinguish and represent the symbols, and the other methods to distinguish and represent the symbols are all within the scope of the present invention.

The identification process of code symbols generally uses template matching method. An embodiment of the present invention takes the 16 kinds of code symbols as the standard match symbols template. Since some code symbols are deformed due to the projection angle in the encoded image of the input symbols, the standard match symbols template can rotate at a small angle around the center of the symbols (location in Step 2) or identify the specific symbols in the encoded image of the input symbols after linear or non-linear transformation of symbols so as to enhance the robustness of the identification. There is another method to use sample training for SVM pattern identification. The exemplary embodiment of the present invention, for each of these 16 kinds of symbols, selects manually or mechanically K groups of correct symbols from the encoded image of the input symbols as samples for training. The above two methods are both exemplary embodiments of the present invention and other identification methods are within the scope of the present invention.

Figure 5:
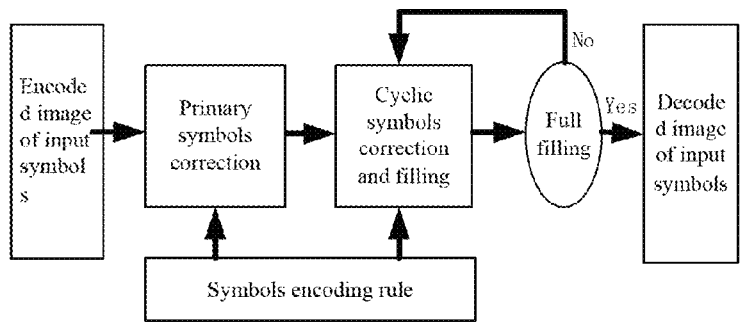
FIG. 5 illustrates a symbols correcting method according to an embodiment of the present invention.

Step 4: symbols correction. The encoded image of the input symbols after symbols recognition follows the symbols coding rule and uses one or more correction and filling to generate the decoded image of the input symbols, as shown in FIG. 5, specifically including:

Step 4.1: primary symbol correction. The encoded image of the input symbols after symbols recognition validates the correctness of the identified symbols, specifically: the identified symbols are validated in combination with its surrounding symbols (one or more symbols at the oblique direction around) and in line with the symbols coding rule. If consistent with the coding rule, the symbols are regarded as the correct one; if not, the symbols are represented with the specific number M as the unidentified one.

Figure 6:
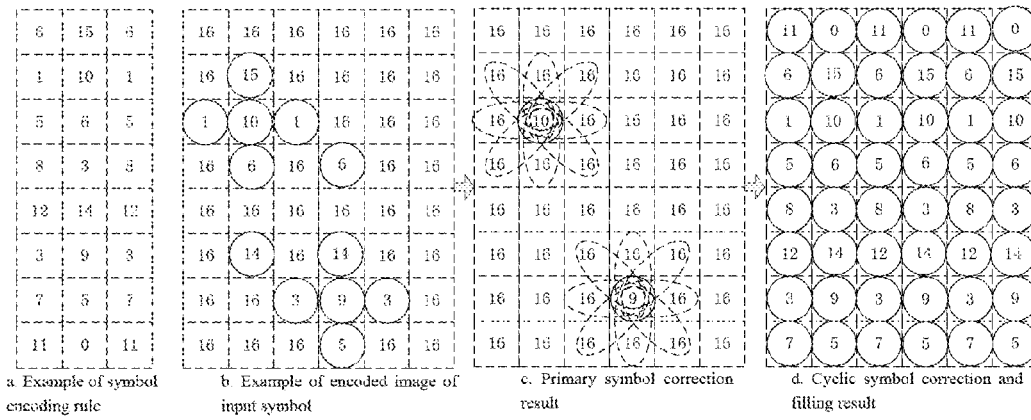
FIG. 6 illustrates a symbols matching method according to an embodiment of the present invention.

FIG. 6 illustrates a correction method according to an embodiment of the present invention. FIG. 6.a shows an example of symbol coding rules. The code symbols are permutated in three columns of numbers corresponding to the symbols, which conforms to a certain encoding rule, and the coding permutation in the decoded image of the reference symbols is consistent with this encoding rule. Any symbols can be determined according to its relationship with surrounding symbols (at the oblique direction around) due to its uniqueness within a certain range at the horizontal or vertical direction. FIG. 6.b shows an example of the encoded image of the input symbols. The number represented with circle is the symbols identified in Step 3, and the symbols represented with the number 16 are the unidentified one. After the primary correction, as shown in FIG. 6.c, the identified symbols in combination with its surrounding symbols (such as four symbols up, down, left and right) and in accordance with the symbols encoding rule is validated, indicating that the corresponding symbols of the numbers 10 and 9 are entirely correct, and the unidentified symbols is represented again with the number 16 as the unidentified one.

Step 4.2: cyclic symbols correction and filling. For the encoded image of the input symbols in Step 4.1, if there is unidentified symbols around the identified one (at the oblique direction around), one or more times of cyclic correction and filling are conducted in line with the symbols encoding rule, and the decoded image of the input symbols identified (i.e. decoded) is finally generated.

As shown in FIG. 6, the cyclic correction and filling of the symbols is conducted, the completely correct symbols are used to expand the unidentified symbols outward according to the symbols encoding rule at eight directions. For example, according to the same symbols encoding rule, the number 1 is on the left and right of the number 10, the number 15 is up, the number 6 is down, the number 6 is on the upper left and upper right, and the number 5 is on the lower left and lower right. With multiple cyclic correction and filling, the correct decoded image of the input symbols is finally output and the decoding process of code symbols is completed.

Step 5: symbols match. The symbols match calculation is performed between the decoded image of the input symbols and the decoded image of the reference symbols of the known distance to generate the corresponding offset of the symbols, i.e. the disparity.

Figure 7:
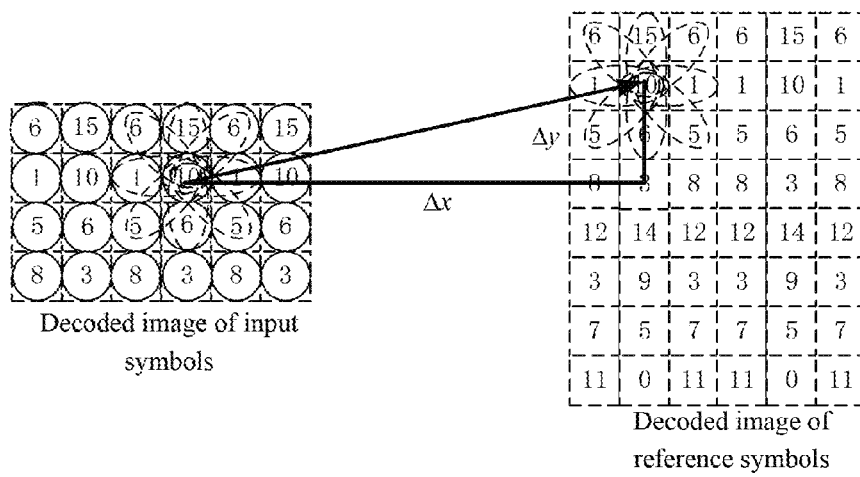
FIG. 7 is a schematic diagram of a disparity value determined after symbols matching according to an embodiment of the present invention.

FIG. 7 is a schematic diagram the disparity determined after symbol matching according to an embodiment of the present invention. The known distance of the decoded image of the reference symbols is d, whose symbols permutation is in line with the encoding rule. As a datum match graphics for the symbols match calculation of the encoded image of the input symbols, it can be constituted by one or more encoded images of laser symbols at different distances. In the decoded image of the input symbols, the symbols 10 search their matched symbols in the decoded image of the reference symbols. The symbols 10 combined with their surrounding symbols (up, down, left, right and diagonally) forms the input symbols template, and shapes of the template include 1×3 window in the vertical direction, five-point window (left, right, up, down and middle), 3×3 window, etc. The closest match symbols of the input symbol template are searched within a certain range of W×H taking the symbols of the corresponding locations of the input symbols in the decoded image of the reference symbols as the center. In the decoded image of the reference symbols, match symbols are successfully searched, and the offset ($\Delta x$, $\Delta y$), namely disparity, between the input symbols and the match symbols is obtained.

Figure 8:
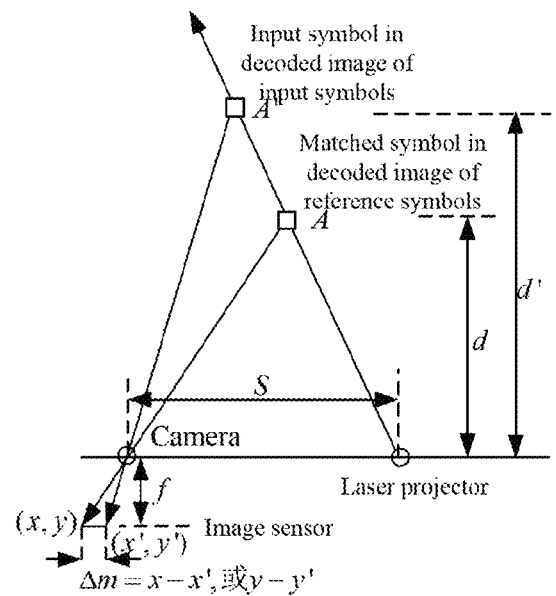
FIG. 8 is a schematic diagram of a symbol depth calculating method according to an embodiment of the present invention.

Step 6: depth calculation. The disparity is combined with the known parameters of the image sensor, and the depth calculation formula is used to obtain the representation in the form of grid and the depth point cloud information of the location of the corresponding symbols. The depth information d' of the center o of the input symbols is calculated according to the following formula by means of the disparity $\Delta m$ ($\Delta x$ or $\Delta y$) at the direction X or Y and in combination with the known distance parameter d of the decoded image of the reference symbols, the baseline distance S between the laser pattern projector and the image sensor, the focal length f and the dot pitch parameter $\mu$ of the image sensor, as shown in FIG. 8.

In the present embodiment, the depth d' is calculated according to the following formula:

$$d' = d - \frac{\Delta m \mu d^2}{fS + \Delta m \mu d} = \frac{fSd}{fS + \Delta m \mu d}$$

The disparity $\Delta m$ is equal to the difference between the x coordinate value of the location of the center of the input symbols of the decoded image of the input symbols and the x' coordinate value of the location of the center of the match symbols of the decoded image of the reference symbols or the difference between the y coordinate value of the location of the center of the input symbols of the decoded image of the input symbols and the y' coordinate value of the location of the center of the match symbols of the decoded image of the reference symbols, positive or negative. The positive disparity $\Delta m$ indicates that it is closer than the distance of the decoded image of the reference symbols and the negative disparity $\Delta m$ indicates that it is farther than the distance of the decoded image of the reference symbols.

Further, the center of the symbols of the decoded image of the input symbols is moved to the next center of the symbols in the same row. Repeat Step 5, and the corresponding depth value of the next center of the symbols is obtained. In this way, the corresponding depth value of all symbols in the encoded image of the input symbols can be calculated one by one (represented with depth point cloud). Similarly, it can also be used to calculate the depth point cloud information of the sequence of the encoded image of the input symbols.

Figure 9:
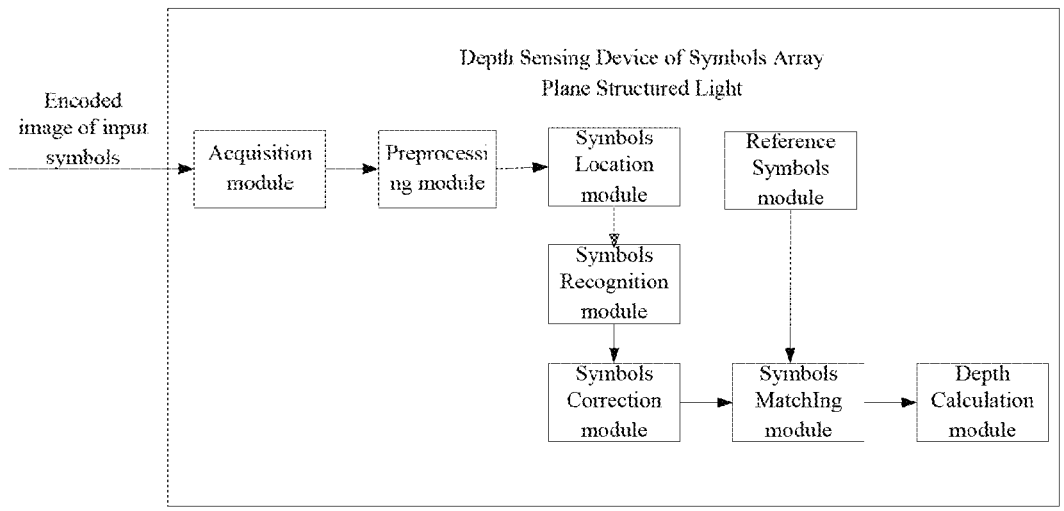
FIG. 9 is another embodiment of the present invention.

FIG. 9 discloses another embodiment of the present invention which relates to a depth sensing device based on symbols array plane structured light, comprising:

An acquisition module acquiring the encoded image of the input symbols of the said symbols array plane structured light;

A preprocessing module used for the adaptive preprocessing of the said encoded image of the input symbols;

A location module used for the symbols location of the preprocessed encoded image of the input symbols to identify the location of the center of all symbols in the encoded image of the input symbols;

An identification module used for the symbols identification of the preprocessed encoded image of the input symbols, mapped to the corresponding number;

A correction module correcting the identified symbols in accordance with the said corresponding number to complete the decoding of the encoded image of the input symbols;

A match module used for the symbols match between the corrected decoded image of the input symbols and the decoded image of the reference symbols of the known distance to generate the corresponding disparity of the symbols;

A determination module determining the depth of the center of symbols in the said encoded image of the input symbols in accordance with the known distance of the decoded image of the reference symbols and the disparity.

Wherein, the location module is used for calculating the location of the center of the said symbols one by one according to the design parameters or determining the location in accordance with the symbols feature information and by means of pattern identification.

Wherein, the identification module by means of template match takes the code symbols as the standard match symbols template rotating at a small angle around the center of the symbols or identifying the code symbols of the encoded image of the input symbols after linear or non-linear transformation of the symbols.

Wherein, the identification module is used to map the correct symbols identified to the specific number N, and the unidentified symbols is represented with the specific number M.

Wherein, the correction module is used to validate the identified symbols combined with its surrounding symbols by means of the encoding rule of the said symbols. The symbols conforming to the said encoding rule is identified as the correct one, while the symbols inconsistent with the coding rule is represented with the specific number M as the unidentified one for further correction, which after cyclic correction and filling generates the corrected decoded image of the input symbols.

Wherein, the said match module is used to search for the closest match symbols of the said input symbols within a certain range taking the symbols of the corresponding location of the input symbols in the decoded image of the reference symbols as the center.

Wherein, the determination module uses the disparity Δm (Δx or Δy) at the direction X or Y which is combined with the known distance parameter d of the decoded image of the reference symbols, the baseline distance S between the laser pattern projector and the image sensor, the focal length f and the dot pitch parameter μ of the image sensor to calculate the depth information d' of the center o of the input symbols according to the following formula:

$$d' = d - \frac{\Delta m \mu d^2}{fS + \Delta m \mu d} = \frac{fSd}{fS + \Delta m \mu d}$$

Figure 10:
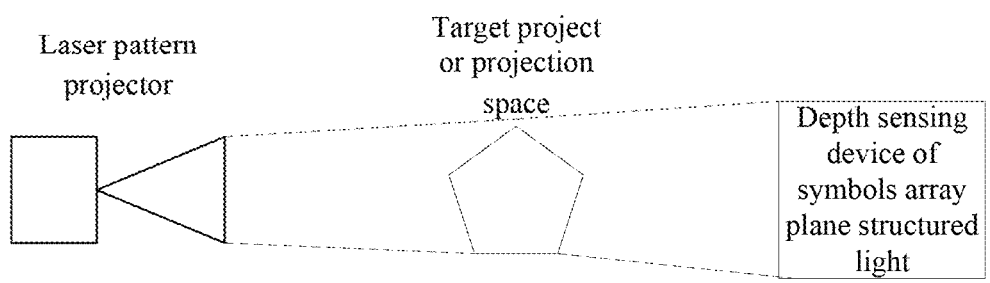
FIG. 10 is another embodiment of the present invention.

FIG. 10 discloses another embodiment of the present invention, which relates to a depth sensing system of symbols array plane structured light, comprising a laser pattern projector and the depth sensing device in the above embodiment, wherein after the encoded graphics is projected by the laser pattern projector to the target object or projection space, the encoded image of the input symbols is received by the depth sensing device.

Although the above embodiments are completed in a particular system, they make no limit to the present invention, and the present invention can be similarly applied to the similar pattern projection and image sensor system; similarly, the decoded image as the match criteria is not limited to single but may be multiple. It will be apparent to those skilled in the art that the present invention is not limited to the above embodiments, and what is described in the above embodiments and specification are merely the illumination of the principle of the present invention. Without deviation from the spirit and scope of the present invention, the present invention will have various changes and improvements, which will be regarded as the inventor's claims to be protected. The scope of protection of the claimed invention is determined by the appended claims and equivalents thereof.

What is claimed is:

1. A depth sensing method of symbols array plane structured light, comprising:
   obtaining the encoded image of the input symbols of the symbols array plane structured light;
   achieving adaptive preprocessing of the encoded image of the input symbols;
   performing symbols location of the preprocessed encoded image of the input symbols to identify the location of the center of all symbols in the coded image of the input symbols;
   conducting symbols recognition of the preprocessed encoded image of the input symbols, mapped as the corresponding number;
   correcting identified symbols in accordance with the corresponding number to complete the decoding of the encoded image of the input symbols;
   making symbols match between the corrected decoded image of the input symbols and the decoded image of the reference symbols of the known distance to generate the corresponding disparity of the symbols;
   determining depth of the center of the symbols in the encoded image of the input symbols in accordance with the known distance of the decoded image of the reference symbols and the disparity,
   wherein making the symbols match between the corrected decoded of the input symbols and the decoded image of the reference symbols of the known distance to generate the corresponding disparity of the symbols, and determining the depth of the center of symbols in the encoded image of the input symbols in accordance with the said known distance and the disparity, comprise:
   the input symbols and their surrounding symbols forming an input symbols template, searching for an optimal match template in a search window of the decoded image of the reference symbols and obtaining the match symbols of the input symbols, so as to obtain the disparity (Δx, Δy) between the input symbols and the match symbols; and
   using the disparity Δm (Δx or Δy) in X or Y direction, in combination with the known distance parameter d of the decoded image of the reference symbols, the baseline distance S between the laser pattern projector and the image sensor, the focal length f and the dot pitch parameter μ of the image sensor, calculating a depth information d' of a center o of the input symbols according to the following formula:

$$d' = d - \frac{\Delta m \mu d^2}{fS + \Delta m \mu d} = \frac{fSd}{fS + \Delta m \mu d}.$$

2. The method according to claim 1, wherein performing the symbols location of the said preprocessed encoded image of the input symbols to identify the location of the center of all symbols in the said coded image of the input symbols, comprises: computing the location of the center of symbols one by one in accordance with the design parameters or determining that in accordance with the feature information of the symbols and by means of pattern identification.

3. The method according to claim 1, wherein the symbols recognition contains a template match method that takes the code symbols as the standard match symbols template rotating at a small angle around the center of the symbols or identifying the code symbols of the encoded image of the input symbols after linear or non-linear transformation of the symbols.

4. The method according to claim 1, wherein the mapping as the corresponding number, comprises: correct symbols identified is mapped on a specific number N, and unidentified symbols is represented with a specific number M.

5. A method described in claim 1, wherein correcting the identified symbols in accordance with the corresponding number comprises validating the identified symbols in combination with its surrounding symbols and by means of coding rule of the said symbols.

6. The method according to claim 5, wherein the symbols conforming to the encoding rule is identified as the correct one, while the symbols inconsistent with the coding rule is represented with the specific number M as the unidentified one for further correction, which after cyclic correction and filling generates the corrected decoded image of the input symbols.

7. The method according to claim 1, wherein the symbols match between the corrected decoded image of the input symbols and the decoded image of the reference symbols of the known distance comprises the search for the closest match symbols of the said input symbols within a certain range taking the symbols of the corresponding location of the input symbols in the decoded image of the reference symbols as the center.

8. The method according to claim 2, wherein the symbols recognition contains a template match method that takes the code symbols as the standard match symbols template rotating at a small angle around the center of the symbols or identifying the code symbols of the encoded image of the input symbols after linear or non-linear transformation of the symbols.

9. The method described in claim 4, wherein correcting the identified symbols in accordance with the corresponding number comprises validating the identified symbols in combination with its surrounding symbols and by means of the coding rule of the said symbols.

10. A depth sensing device for symbols array plane structured light, comprising:

an acquisition module acquiring the encoded image of the input symbols of the symbols array plane structured light;

a preprocessing module, used for the adaptive preprocessing of the said encoded image of the input symbols;

a symbols location module used for the symbols location of the preprocessed encoded image of the input symbols to identify the location of the center of all symbols in the encoded image of the input symbols;

a symbols recognition module, used for the symbols recognition of the preprocessed encoded image of the input symbols, mapped to the corresponding number;

a symbols correction module, used for correcting the identified symbols in accordance with the corresponding number to complete the decoding of the encoded image of the input symbols;

a symbols match module, used for the symbols match between the corrected decoded image of the input symbols and the decoded image of the reference symbols a known distance to generate a corresponding disparity of the symbols;

a depth calculation module, used for determining the depth of the center of symbols in the encoded image of the input symbols in accordance with the known distance of the decoded image of the reference symbols and the disparity, wherein the determination module uses the disparity $\Delta m$ ($\Delta x$ or $\Delta y$) at the direction X or Y and combines with the known distance parameter d of the decoded image of the reference symbols, the baseline distance S between the laser pattern projector and the image sensor, the focal length f and the dot pitch parameter $\mu$ of the image sensor to calculate the depth information d' of the center o of the input symbols according to the following formula:

$$d' = d - \frac{\Delta m \mu d^2}{fS + \Delta m \mu d} = \frac{fSd}{fS + \Delta m \mu d}.$$

11. The device according to claim 10, wherein said location module is used for calculating the location of the center of the said symbols one by one according to the design parameters or determining the location in accordance with the symbols feature information and by means of pattern identification.

12. The device according to claim 11, wherein said symbols recognition module by means of template match takes the code symbols as the standard match symbols template rotating at a small angle around the center of the symbols or identifying the code symbols of the encoded image of the input symbols after linear or non-linear transformation of the symbols.

13. The device according to claim 10, wherein said symbols recognition module by means of template match takes the code symbols as the standard match symbols template rotating at a small angle around the center of the symbols or identifying the code symbols of the encoded image of the input symbols after linear or non-linear transformation of the symbols.

14. The device according to claim 10, wherein said symbols recognition module is used to map the correct symbols identified with a specific number N, and the unidentified symbols is represented with a specific number M.

15. The device according to claim 10, wherein the correction module is used to validate the identified symbols combined with its surrounding symbols by means of the encoding rule of the symbols, the symbols conforming to the said encoding rule is identified as the correct one; while the symbols inconsistent with the coding rule is represented with the specific number M as the unidentified one for further correction, which after cyclic correction and filling generates the corrected decoded image of the input symbols.

16. The device according to claim 10, wherein the match module is used to search for the closest match symbols of the input symbols within a certain range taking the symbols of the corresponding location of the input symbols in the decoded image of the reference symbols as the center.

17. A depth sensing system based on symbols array plane structured light, comprising a laser pattern projector and a depth sensing device according to claim 10, wherein after the laser pattern projector projects coded graphics to the target object or the projection space, the depth sensing device receives the encoded image of the input symbols.

* * * * *